(12) United States Patent
Vitaris

(10) Patent No.: US 8,257,326 B2
(45) Date of Patent: Sep. 4, 2012

(54) APPARATUS FOR ENHANCING WOUND HEALING

(75) Inventor: Ronald F. Vitaris, Worcester, MA (US)

(73) Assignee: Tyco Healthcare Group LP, Mansfield, MA (US)

(*) Notice: Subject to any disclaimer, the term of this patent is extended or adjusted under 35 U.S.C. 154(b) by 452 days.

(21) Appl. No.: 12/490,797

(22) Filed: Jun. 24, 2009

(65) Prior Publication Data
US 2009/0326487 A1 Dec. 31, 2009

Related U.S. Application Data

(60) Provisional application No. 61/076,753, filed on Jun. 30, 2008.

(51) Int. Cl.
*A61F 13/00* (2006.01)
(52) U.S. Cl. .......................... 604/305; 604/23
(58) Field of Classification Search ................. 604/305, 604/19, 23, 289, 304, 307, 317, 504; 424/445; 602/43
See application file for complete search history.

(56) References Cited

U.S. PATENT DOCUMENTS

| | | | |
|---|---|---|---|
| 3,081,771 A * | 3/1963 | Lee | 604/344 |
| 3,367,332 A | 2/1968 | Groves | |
| 3,486,504 A | 12/1969 | Austin, Jr. | |
| 3,572,340 A | 3/1971 | Lloyd et al. | |
| 3,712,298 A | 1/1973 | Snowdon et al. | |
| 3,809,086 A | 5/1974 | Schachet et al. | |
| 3,874,387 A | 4/1975 | Barbieri | |
| 4,080,970 A | 3/1978 | Miller | |
| 4,112,947 A | 9/1978 | Nehring | |
| 4,112,949 A | 9/1978 | Rosenthal et al. | |
| 4,136,696 A | 1/1979 | Nehring | |
| 4,202,331 A * | 5/1980 | Yale | 602/53 |
| 4,224,945 A * | 9/1980 | Cohen | 606/201 |
| 4,266,545 A | 5/1981 | Moss | |
| 4,382,441 A | 5/1983 | Svedman | |
| 4,524,064 A | 6/1985 | Nambu | |
| 4,710,165 A | 12/1987 | McNeil et al. | |
| 4,738,257 A * | 4/1988 | Meyer et al. | 602/48 |
| 4,743,232 A | 5/1988 | Kruger | |

(Continued)

FOREIGN PATENT DOCUMENTS
DE 41 11 122 A1 4/1993
(Continued)

OTHER PUBLICATIONS

International Search Report Application No. PCT/US2009/048580 dated Aug. 17, 2009.

(Continued)

*Primary Examiner* — Tatyana Zalukaeva
*Assistant Examiner* — Benedict L Hanrahan

(57) ABSTRACT

A wound therapy apparatus for enhancing healing of a wound includes a wound dressing configured for placement over the wound to define a reservoir over the wound in which a wound contact fluid may be maintained by forming a substantially fluid-tight seal around the wound. An elastic bladder member defined by or within the wound dressing is expandable to exert a pressure on the wound contact fluid within the reservoir. A fluid system is in fluid communication with the reservoir for selectively delivering the wound contact fluid to the reservoir, and a pressure system is in fluid communication with the bladder member for delivering a compressed liquid or gas to the bladder member to effect expansion in the bladder member.

7 Claims, 3 Drawing Sheets

U.S. PATENT DOCUMENTS

| | | |
|---|---|---|
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,195,977 A | 3/1993 | Pollitt |
| 5,261,893 A | 11/1993 | Zamierowski |
| 5,263,922 A | 11/1993 | Sova et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,779,657 A | 7/1998 | Daneshvar |
| 5,840,049 A | 11/1998 | Tumey et al. |
| 5,911,222 A | 6/1999 | Lawrence et al. |
| 5,944,703 A | 8/1999 | Dixon et al. |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0143286 A1 | 10/2002 | Tumey |
| 2002/0151836 A1 | 10/2002 | Burden |
| 2002/0161346 A1 | 10/2002 | Lockwood et al. |
| 2003/0078532 A1 | 4/2003 | Ruszczak et al. |
| 2003/0093041 A1 | 5/2003 | Risk, Jr. et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0064132 A1 | 4/2004 | Boehringer |
| 2004/0073151 A1 | 4/2004 | Weston |
| 2004/0093026 A1 | 5/2004 | Weidenhagen et al. |
| 2004/0113309 A1* | 6/2004 | Thompson et al. ........ 264/210.8 |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0243073 A1 | 12/2004 | Lockwood et al. |
| 2004/0249353 A1 | 12/2004 | Risk, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1 | 11/2005 | Weston |
| 2005/0261643 A1 | 11/2005 | Bybordi et al. |

| | | | |
|---|---|---|---|
| 2006/0015087 A1 | 1/2006 | Risk, Jr. et al. | |
| 2006/0025727 A1 | 2/2006 | Boehringer et al. | |
| 2006/0029650 A1 | 2/2006 | Coffey | |
| 2006/0039742 A1 | 2/2006 | Cable, Jr. et al. | |
| 2006/0041247 A1 | 2/2006 | Petrosenko et al. | |
| 2006/0079852 A1 | 4/2006 | Bubb et al. | |
| 2006/0100586 A1 | 5/2006 | Karpowicz et al. | |
| 2006/0100594 A1 | 5/2006 | Adams et al. | |
| 2006/0116620 A1 | 6/2006 | Oyaski | |
| 2006/0149170 A1 | 7/2006 | Boynton et al. | |
| 2007/0005028 A1 | 1/2007 | Risk, Jr. et al. | |
| 2007/0014837 A1 | 1/2007 | Johnson et al. | |
| 2007/0016152 A1 | 1/2007 | Karpowicz | |
| 2007/0021697 A1 | 1/2007 | Ginther et al. | |
| 2007/0027414 A1 | 2/2007 | Hoffmann et al. | |
| 2007/0032754 A1 | 2/2007 | Walsh | |
| 2007/0032755 A1 | 2/2007 | Walsh | |
| 2007/0032778 A1 | 2/2007 | Heaton et al. | |
| 2007/0055209 A1 | 3/2007 | Patel et al. | |
| 2007/0066946 A1 | 3/2007 | Haggstrom et al. | |
| 2007/0078366 A1 | 4/2007 | Haggstrom et al. | |
| 2007/0167927 A1 | 7/2007 | Hunt et al. | |
| 2007/0179460 A1 | 8/2007 | Adahan | |
| 2007/0185426 A1 | 8/2007 | Ambrosio et al. | |
| 2007/0225663 A1 | 9/2007 | Watt et al. | |
| 2007/0233022 A1* | 10/2007 | Henley et al. | 604/305 |
| 2008/0071235 A1 | 3/2008 | Locke et al. | |
| 2008/0200857 A1 | 8/2008 | Lawhorn | |
| 2008/0200906 A1 | 8/2008 | Sanders et al. | |
| 2008/0208147 A1 | 8/2008 | Argenta et al. | |
| 2008/0234641 A1 | 9/2008 | Locke et al. | |

FOREIGN PATENT DOCUMENTS

| | | |
|---|---|---|
| DE | 295 04 378 U1 | 10/1995 |
| EP | 0 020 662 B1 | 7/1984 |
| EP | 0 358 302 | 3/1990 |
| EP | 1088589 | 4/2001 |
| EP | 1219311 | 7/2002 |
| EP | 0 853 950 B1 | 10/2002 |
| GB | 1 549 756 | 3/1977 |
| GB | 2 195 255 A | 4/1988 |
| GB | 2 235 877 A | 3/1991 |
| GB | 2307180 | 5/1997 |
| GB | 2329127 | 3/1999 |
| GB | 2336546 | 10/1999 |
| GB | 2344531 | 6/2000 |
| GB | 2 415 908 | 1/2006 |
| SU | 1762940 | 1/1989 |
| WO | 80/01139 | 6/1980 |
| WO | 80/02182 | 10/1980 |
| WO | 84/01904 | 5/1984 |
| WO | 89/05133 | 6/1989 |
| WO | 90/11795 | 10/1990 |
| WO | 92/19313 | 11/1992 |
| WO | 93/09727 | 5/1993 |
| WO | 94/20041 | 9/1994 |
| WO | 96/05873 | 2/1996 |
| WO | 9605873 | 2/1996 |
| WO | 00/21586 | 4/2000 |
| WO | 03/005943 | 1/2003 |
| WO | 03/018098 | 3/2003 |
| WO | 03/030966 | 4/2003 |
| WO | 03/057070 | 7/2003 |
| WO | 03/057307 | 7/2003 |
| WO | 03057307 | 7/2003 |
| WO | 03/045492 | 8/2003 |
| WO | 03/086232 | 10/2003 |
| WO | 03/092620 | 11/2003 |
| WO | 03101508 | 12/2003 |
| WO | 2004018020 | 3/2004 |
| WO | 2005009488 | 2/2005 |
| WO | 2006/105892 | 10/2006 |

OTHER PUBLICATIONS

US 7,186,244, Mar. 6, 2007, Hunt et al., (withdrawn).
US 6,216,701, Apr. 17, 2001, Heaton et al., (withdrawn).

Meyer, M.D., et al., "In Surgery, Medicine and the Specialties A Manual of its Practical Application", Bier's Hyperemic Treatment, Second Revised Edition, W.B. Saunders Company, 1909.
Jeter, Katherine F., et al., "Managing Draining Wounds and Fistulae: New and Established Methods", Chronic Wound Care, 1990, pp. 240-246.
Chariker, M. E. et al. (eds), "Effective Management of Incisional and Cutaneous Fistulae with Closed Suction Wound Drainage," Contemporary Surgery, vol. 34, Jun. 1989, pp. 59-63.
B.M. Kostiuchenok, et al., "The Vacuum Effect in the Surgical Treatment of Purulent Wounds," Russian Journal: Vestnik Khirurgii, Sep. 1986., (18-21).
Y.N. Usupov, et al., "Active Wound Drainage," Russian Journal: Vestnik Khirugii, Apr. 1987, (42-45).
Yu A. Davydov, et al., "Concepts for Clinical Biological Management of the Wound Process in the Treatment of Purulent Wounds Using Vacuum Therapy," Vestnik Khirugii, Feb. 1991, 132-135).
N.A. Bagautdinov (Kazan), "Variant of External Vacuum Aspiration in the Treatment of Purulent Diseases of Soft Tissues," UDC 616-002.36 (94-96).
Chardack, et al., "Experimental studies on Synthetic Substitutes for Skin and Their Use in the Treatment of Burns," vol. 155, No. 1 (128-136).
Gorica Zivadinovic, et al., "Vacuum Therapy in the Treatment of Peripheral Blood Vessels," Conference Papers of the 5th Timok Medical Days, Majdanpek, 1986 (161-164).
Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).
W. Fleischmann, et al., Vacuum Sealing: Indication, Technique and Results, Emr J Orthop Surg Tramatol (1995) 5:37-40.
Sherry Stoll, "Energetic Remedies—Cupping: Healing Within a Vacuum," https://www.suite101.com/article.cfm/energetic)remedies/74531, Apr. 13, 2005.
Mulder, G.D, et al., "Clinicians' Pocket Guide to Chronic Wound Repair," Wound Healing Publications Second Edition, 1991.
Yu A. Davydov, et al., "Vacuum Therapy in the Treatment of Purulent Lactation Mastitis," Russian Journal: Vesnik Khirurgii, Sep. 1986, (66-70).
Yu A. Davydov, et al., "Bacteriological and Cytological Assessment of Vacuum Therapy of Purulent Wounds", Vestnik Khirurgii, Oct. 1988, (48-52).
W. Fleischmann, "Vacuum Sealing for Treatment of Problematical Wounds", University Surgical Clinic and Polyclinic—Accident Surgery Department, WundForum Spezial—IHW 94.
Göran Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Björn, et al., "Irrigation Treatment in Split-thickness Skin Grafting of Intractable Leg Ulcers," Scand J Plast Reconstr Surg 19: 211-213, 1985.
Paul Svedman, et al., "Staphylococcal Wound Infection in the Pig: Part I. Course," Annals of Plastic Surgery, vol. 23, No. 3, Sep. 1989 (212-218).
Paul Svedman, "A Dressing Allowing Continuous Treatment of a Biosurface," IRCS Medical Science: Biomedical Technology; Clinical Medicine; Surgery and Transplantation, 7, 221 (1979).
Paul Svedman, "Irrigation Treatment of Leg Ulcers," The Lancet, Sep. 3, 1983 (532-534).
H. Teder, et al., "Continuous Wound Irrigation in the Pig," Journal of Investigative Surgery, vol. 3 (399-407).
P. Svedman, "A Dressing System Providing Fluid Supply and Suction Drainage Used for Continuous or Intermittent Irrigation," Annals of Plastic Surgery, vol. 17, No. 2, Aug. 1986 (125-133).
Yu A. Davydov, et al., "Vacuum Therapy in treatment of Acute Purulent Diseases of Soft Tissues and Purulent Wounds," Vestnik Khirurgii, (Surgeon's Herald), MEDICINE Publishers, 1986.

* cited by examiner

APPARATUS FOR ENHANCING WOUND HEALING

CROSS REFERENCE TO RELATED APPLICATIONS

The present invention claims the benefit of and priority to U.S. provisional patent application Ser. No. 61/076,753 filed on Jun. 30, 2008, disclosure of which may be referred to herein by reference.

BACKGROUND

1. Technical Field

The present disclosure relates generally to an apparatus for generating and maintaining an environment around a wound to enhance healing of the wound. In particular, the disclosure relates to an apparatus including a fluid system for providing a fluid to the wound and dressing for providing a pressure to the fluid.

2. Background of Related Art

The body's natural wound healing process is a complex series of events beginning at the moment of injury. Initially the body reacts by delivering proteins and other factors to the wound through the blood stream to minimize the damage. Blood clots to prevent blood loss while cells engulf bacteria and debris to carry it away from the wound site. Next, the body begins to repair itself in a stage of healing often referred to as the "proliferate" phase. This phase is characterized by the deposition granulation tissue in the wound bed. Granulation tissue provides a base structure over which cells may migrate inwardly from the periphery to close the wound. Finally the process ends as collagen gives strength to new tissue over time often forming a scar.

Throughout the healing process, the body has a natural tendency to break down dead tissue and debris, thereby cleaning the wound and allowing new cells to form. This natural process is often referred to as autolytic debridement. One technique for promoting autolytic debridement, and wound healing generally, involves the application of a pressure to a wound. The application of both positive and negative pressures to a wound has proven effective in closing and healing the wound by promoting blood flow to the area, stimulating the formation of granulation tissue and the migration of healthy tissue over the wound by the natural process. Also, reduced pressures may assist in removing fluids exuding from the wound, which may inhibit bacterial growth. These techniques have proven effective for chronic or non-healing wounds, but have also been used for other purposes such as post-operative wound care.

The application of pressure to a wound may be facilitated by an apparatus permitting the environment around the wound to be controlled. Accordingly, an apparatus defining a reservoir around a wound where a pressure may be controlled may prove beneficial.

SUMMARY

The present disclosure describes an apparatus for enhancing healing of a wound. The apparatus includes a wound dressing configured for placement over the wound to define a reservoir over the wound in which a wound contact fluid may be maintained by forming a substantially fluid-tight seal around the wound. An elastic bladder member defined by or within the wound dressing is expandable to exert a pressure on the wound contact fluid within the reservoir. A fluid system is in fluid communication with the reservoir for selectively delivering the wound contact fluid to the reservoir, and a pressure system is in fluid communication with the bladder member for delivering a compressed liquid or gas to the bladder member to effect expansion in the bladder member.

The elastic bladder member may be coupled to a substantially inelastic backing layer and the backing layer may be coupled to a body attachment layer for contacting the skin around the wound. Expansion of the bladder member may then effect a tension in backing layer to the draw the skin around the wound inwardly. The elastic bladder member may be coupled to the substantially inelastic backing layer by an inner adhesive ring nested within an outer adhesive ring. The inner adhesive ring may encircle a fluid communication portal providing fluid communication between the reservoir and the fluid system.

Alternatively, the elastic bladder member may be coupled to an elastic backing layer and the backing layer may be coupled to a reinforcement layer providing bilateral stiffness to the dressing. The reinforcement layer may comprise a mesh formed from polyethylene terephthalate fibers, and the backing layer may be constructed from urethane.

The wound contact fluid may comprise a medicament to promote wound healing such as a debridement agent, an antimicrobial agent, polyhexamethylene biguanide, an antibiotic, a growth factor or an analgesic. The fluid system may comprise a syringe repeatably detachable from the apparatus.

According to another aspect of the disclosure, a wound dressing for enhancing healing of a wound includes a substantially elastic backing layer configured for placement over a wound to define a reservoir over the wound in which a wound contact fluid may be maintained by forming a substantially fluid-tight seal around the wound. A reinforcement layer is adhered to the backing layer for providing a bilateral stiffness to the wound dressing and extends to a peripheral region of the backing layer. An elastic bladder member defined by or within the wound dressing is expandable to exert a pressure on the wound contact fluid within the reservoir. The elastic bladder member includes a fluid communication port therethrough to permit introduction of the wound contact fluid to the wound. The backing layer may be coupled to a portal member, which includes a central bore to permit introduction of the wound contact fluid and a distinct interior distribution ring to permit introduction to a compressible liquid or gas to a pressure application zone of the bladder member.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
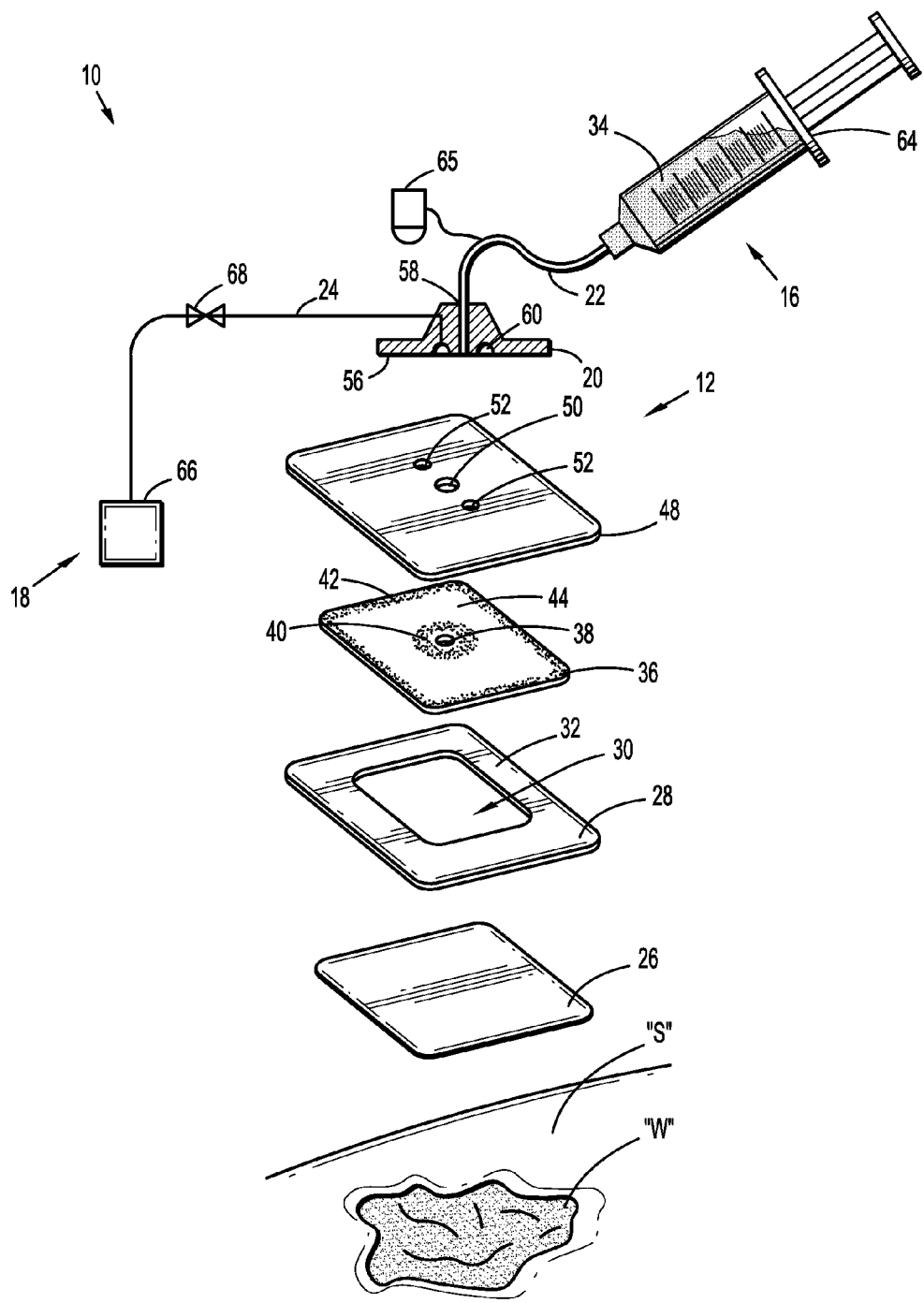
FIG. 1 is an exploded perspective view of a wound therapy apparatus in accordance with the present disclosure.
Figure 2:
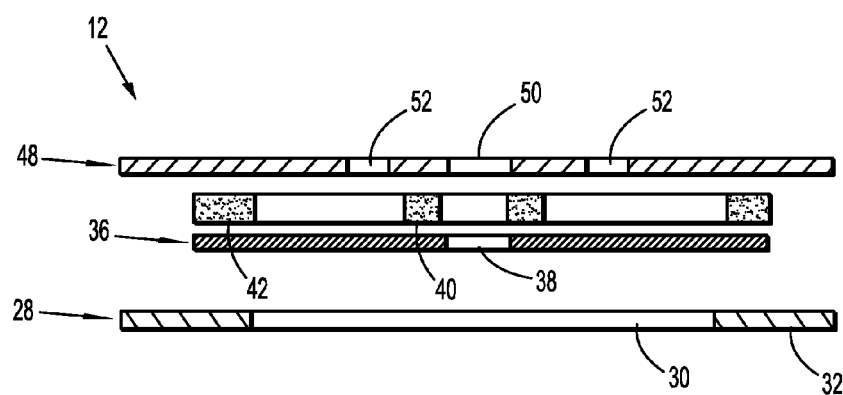
FIG. 2 is an exploded cross sectional view of the wound dressing of FIG. 1.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Referring initially to FIG. 1, a wound therapy apparatus according to the present disclosure is depicted generally as 10 for use on a wound "w" surrounded by healthy skin "s." The apparatus 10 includes a wound dressing 12 for placement over the wound "w" to define a reservoir 14 (FIG. 3) over the wound in which a fluid may be maintained. The apparatus 10 also includes a fluid system 16 in fluid communication with the reservoir 14, and a pressure system 18 in fluid communication with the wound dressing 12. A portal member 20 provides a mechanism for connecting various fluid conduits 22, 24 to the wound dressing 12 to facilitate fluid communication with the fluid system 16 and pressure system 18.

The wound dressing 12 is a composite dressing formed from the lamination or juxtaposition of several distinct layers. First, a release paper 26 is positioned at a distal or wound facing side of the dressing 12. The release paper 26 is configured to protect the dressing 12 prior to the application of the dressing 12 to the wound "w," and may be removed from the dressing 12 and discarded just before the dressing 12 is applied. Release paper 26 need not be constructed of paper, but may be formed from any suitable material including polyurethane, metallic foils, polyolefins and polyesters.

Positioned on a proximal side of the release paper 26 is a body attachment layer 28. The body attachment layer 28 includes a central opening 30 extending laterally beyond the perimeter of the wound "w" such that a body attachment adhesive 32 may contact the healthy skin "s" to form a seal around the wound "w." To form an appropriate seal, body attachment adhesive 32 may be constructed from a medical-grade, pressure-sensitive adhesive adapted to provide a fluid-tight and bacteria-tight seal around a peripheral region of the dressing 12. In this manner, wound contact fluids 34 (see FIG. 3) will not tend to escape through the edges of the dressing 12, and external contaminants may not enter the wound area. To provide such a barrier, the body attachment adhesive 32 may, for example, be on the order of 1.0 to 10 mils thick depending on the adhesive used. In general, a high peal-strength adhesive may be used to resist inadvertent lift-off, roll or "flagging," i.e., a failure of the dressing to adhere to itself or the skin "s," at the edges of the dressing. The adhesive defining body attachment adhesive layer 32 may include, but is not limited to, medical grade acrylics, rubber base or silicone adhesives. Preferably, those adhesives included with the dressing sold under the trademark POLYSKIN®II offered by Tyco Healthcare Group LP (d/b/a Covidien) may be used.

Positioned within the central opening 30 of the body attachment layer 28 is a bladder member 36. Alternatively, bladder member 36 can be positioned upon body attachment layer 28 to cover or traverse central opening 30. Bladder member 36 is constructed of an elastically deformable elastomer or similar material, and includes a fluid communication portal 38 extending through a central region. An upper surface of the bladder member 36 includes nested rings 40, 42 of a permanent adhesive thereon. An inner ring 40 encircles the fluid communication portal 38 in the central region while outer ring 42 extends to a periphery of the bladder member 36. A pressure application zone 44 is defined between the two nested rings 40, 42.

Disposed over the bladder member 36 is a backing layer 48. Backing layer 48 is substantially inelastic relative to the bladder member 36 and may be constructed from a flexible polymeric membrane. For example, backing layer 48 may comprise a polyurethane film having a thickness from about 0.8 mils to about 1.0 mil. A membrane that provides a sufficient moisture vapor transmission rate (MVTR) is a transparent membrane sold under the trade name POLYSKIN®II offered by Tyco Healthcare Group LP (d/b/a Covidien). Other materials which may be suitable for use in a backing layer include the thin films marketed under the names TEGADERM™ by 3M of St. Paul, Minn. and OPSITE™ by Smith and Nephew PLC of London, UK.

The backing layer 48 adheres to the bladder member 36 due to contact with the nested adhesive rings 40, 42. A fluid hole 50 extends through backing layer 48 in general alignment with the fluid communication portal 38 of the bladder member 36. A pair of pressure supply holes 52 flank the fluid hole 50 such that the pressure supply holes 52 communicate with the pressure application zone 44 of the bladder member 36. The inner adhesive ring 40 extends between the fluid hole 50 and the pressure supply holes 52 such that the fluid hole 50 and the pressure supply holes 52 are fluidly distinct. The backing layer 48 also adheres to the body attachment layer 28 such that the dressing 12 may form a reservoir 14 over the wound "w."

Portal member 20 adheres to an upper surface of the backing layer 48 in a substantially fluid tight manner. A suitable adhesive 56 is disposed about a perimeter of on an underside of the portal member 20 to facilitate this connection. Alternatively, an adhesive may be disposed on the upper surface of the backing layer 48, or other fluid tight arrangements may be appropriate. Portal member 20 includes a hollow central bore 58, which provides fluid communication between the fluid hole 50 and the fluid conduit 22 leading to the fluid system 16. Portal member 20 also includes a distinct interior air distribution ring 60, which provides fluid communication between the pressure supply holes 52 and the fluid conduit 24 leading to the pressure system 18. Portal member 20 may include check valves (not shown) within the central bore 58 and the distribution ring 60 for retaining fluids within the reservoir 14 and pressure application zone 44.

The fluid system 16 is in fluid communication with the reservoir 14 as described above. Fluid system 16 serves to evacuate the reservoir 14 and also to supply the reservoir 14 with wound contact fluid 34. The wound contact fluid 34 is generally a low viscosity fluid such that it may conform to the particular geometry of the wound "w," and may adapt as the geometry of the wound "w" changes during healing. The wound contact fluid 34 may include a beneficial agent such as a medicament to promote wound healing. Medicaments include, for example, antimicrobial agents, polyhexamethylene biguanide, growth factors, antibiotics, analgesics, and the like. Suitable medicaments also include debridement agents such as chemical compounds or enzymes that intimately surround and infiltrate necrotic tissue.

Fluid system 16 comprises a syringe 64 to deliver the wound contact fluid 34. Syringe 64 may be repeatably removable and connectable to the apparatus 10 through a standard luer connection, for example. Syringe 64 may therefore be connected to the apparatus 10 in an empty state to evacuate the reservoir 14, and may then be disconnected so that it may be filled with wound contact fluid 34. Once filled with wound contact fluid 34, syringe 64 may be reattached to the apparatus as shown to deliver the wound contact fluid 34 to the reservoir 14. Alternatively, the fluid system 16 may comprise multiple syringes, a reversible electric pump, or a similar mechanism to manage the contents of the reservoir 14. A collection canister 64 is selectively coupled to fluid conduit 22 to receive any wound exudates or debris during evacuation of the reservoir 14. Collection canister 64 is removable such that wound contact fluid 34 need not flow into or through the canister 64 as the wound contact fluid 34 is delivered to the reservoir 14.

The pressure system 18 is in fluid communication with the pressure application zone 44 of the bladder member 36. A pressure source 66 is coupled to the pressure application zone 44 through fluid conduit 24, a valve 68, and portal member 20 such that the pressure source 66 may selectively supply a pressurized liquid or gas, air for example, to the pressure application zone 44. Pressure source 26 may be configured to provide the pressurized liquid or gas in a continuous or intermittent fashion.

Figure 3:
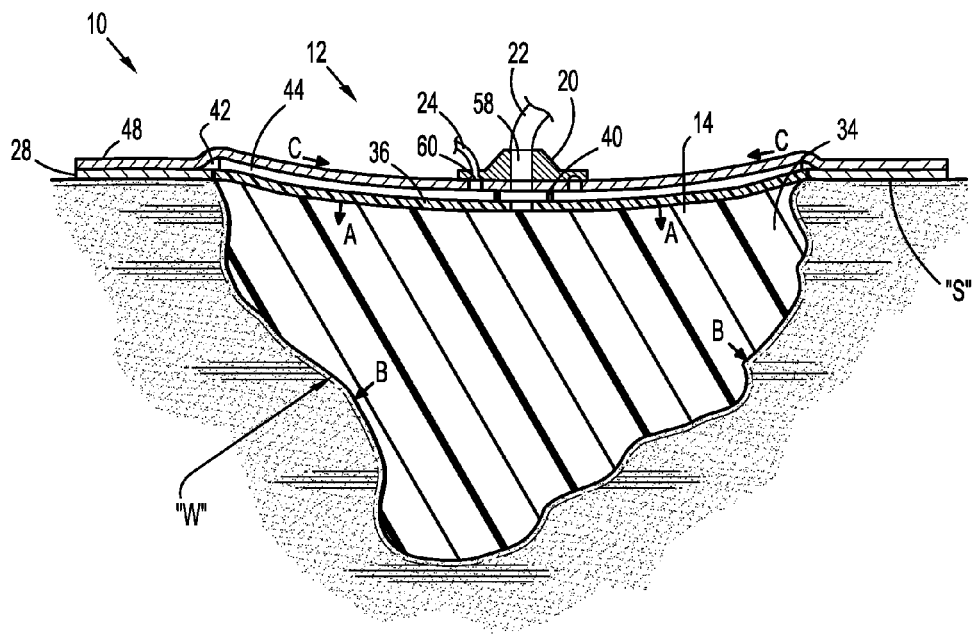
FIG. 3 is a cross sectional view of the wound dressing of FIG. 1 applied on a wound.

In use, wound therapy apparatus 10 may be used to apply a pressure to the wound "w" as depicted in FIG. 3. The wound dressing 12 is applied to the skin "s" around the wound "w" defining reservoir 14. Ambient air captured beneath the dressing 12 is evacuated and wound contact fluid 34 is delivered to the reservoir by fluid system 16. Pressure system 18 delivers the pressurized liquid or gas to the pressure application zone 44 of the bladder member 36 such that the bladder member 36 applies a pressure to the wound contact fluid 34 as indicated by arrows "A." The wound contact fluid 34 conforms to geometry of the wound "w" and delivers an effective pressure to wound "w" to stimulate healing of the wound as indicated by arrows "B." An effective pressure may, for example, induce cellular surface strain within the wound in the range of from about 5 to about 20 percent.

As used in this manner, dressing 12 may also serve to promote closure of the wound "w." Bladder member 36 may stretch to accommodate the application of pressure to the pressure application zone 44. Since the backing layer 48 is substantially inelastic relative to the bladder member 36, reactionary forces in the backing layer may exert an inwardly directed force on the margins of the wound "w" as indicated by arrows "C."

Figure 4:
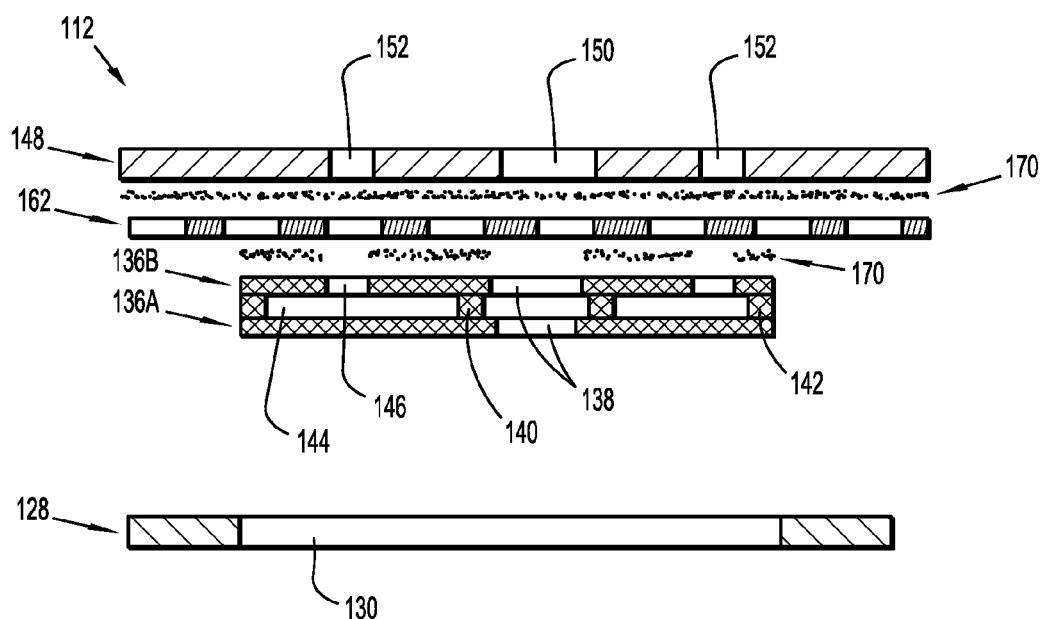
FIG. 4 is an exploded cross sectional view of an alternate embodiment of a wound dressing in accordance with the present disclosure.

Referring now to FIG. 4, an alternate embodiment of a wound dressing in accordance with the present disclosure is depicted generally as 112. Wound dressing 112 includes a body attachment layer 128 for forming a fluid tight seal with the skin "s" surrounding wound "w." Positioned within a central opening 130 of the body attachment layer 128 or overlapping a portion of body attachment layer 128 is a lower bladder member 136A. Lower bladder member 136A includes a fluid communication portal 138 to permit the introduction of wound contact fluid 34 to the wound "w." An upper bladder member 136B is coupled to the lower bladder member 136A by nested adhesive rings 140, 142. The upper bladder member 136B includes a fluid communication portal 138 as well as pressure supply holes 146 in communication with a pressure application zone 144. Both upper and lower bladder members 136A and 136B may be elastic and stretch under the application of pressure from pressure system 18. At an upper surface of dressing 112, backing layer 148 may be constructed of a relatively elastic material such as urethane. Backing layer 148 includes a fluid hole 150 and pressure supply holes 152 to provide fluid communication to the reservoir 14 and pressure application zones 144 respectively.

Disposed between upper bladder member 136B and backing layer 148 is a reinforcement layer 162 providing a bilateral stiffness to the dressing 112. Reinforcement layer 162 may overlap body attachment layer 128 at an outer edge of the dressing 112 such that reactionary forces generated in the dressing 112 may be directed to the skin "s" surrounding the wound "w." Reinforcement layer 162 may be affixed to backing layer 148 with a light coat of an adhesive 170 applied to the appropriate side of the reinforcement layer 162 or the backing layer 148. Reinforcement layer 162 may be also be affixed to upper bladder member 136B with a light coat of an adhesive 170 applied to the appropriate side of the reinforcement layer 162 or the upper bladder member 136B.

The reinforcement layer 162 may comprise a mesh of polyethylene terephtalate (PET) fibers, which offer good liquid resistance making it suitable for use in a moist wound environment. PET fibers may be used to form woven or nonwoven reinforcements having large pore sizes. Some PET reinforcement manufacturing methods provide for interlinking the fiber junctions to yield a mesh that is flexible in multiple directions and also does not unravel when cut. PET reinforcements thus manufactured tend to have a high shear stiffness that may be useful in reinforcing backing layer 148 and providing a bilateral stiffness to dressing 112. One exemplary material, which may be suitable for incorporation into reinforcement layer 162, is sold under the trademark Sontara® by DuPont. Alternatively, reinforcement layer 162 may be formed from another reinforcement or mesh structure having suitable shear stiffness. Examples of suitable structures include extruded thermoplastic netting and apertured films. Suitable materials for use in such alternate structures include PET, polyethylene, nylon and polypropylene. Additionally, woven structures may be used for reinforcement layer 162. Acceptable woven materials may include cotton gauze, woven acetate and nylon.

Although the foregoing disclosure has been described in some detail by way of illustration and example, for purposes of clarity or understanding, it will be obvious that certain changes and modifications may be practiced within the scope of the appended claims.

What is claimed is:

1. A wound therapy apparatus for enhancing healing of a wound, comprising:
    a wound dressing configured for placement over a wound to define a reservoir over the wound in which a wound contact fluid may be maintained by forming a substantially fluid-tight seal around the wound;
    an elastic bladder member defined by or within the wound dressing and coupled to a substantially inelastic backing layer by an inner adhesive ring nested within an outer adhesive ring, the outer adhesive ring being independent of, and spaced from, the inner adhesive ring, the elastic bladder member being expandable to exert a pressure on the wound contact fluid within the reservoir;
    a fluid system in fluid communication with the reservoir for selectively delivering the wound contact fluid to the reservoir; and
    a pressure system in fluid communication with a pressure application zone defined between the inner and outer adhesive rings of the bladder member for delivering a compressed liquid or gas to the pressure application zone of the bladder member to effect expansion in the bladder member.

2. The apparatus according to claim 1, wherein the backing layer is coupled to a body attachment layer for contacting the skin around the wound such that expansion of the bladder member may effect a tension in backing layer to the draw the skin around the wound inwardly.

3. The apparatus according to claim 1, wherein the inner adhesive ring encircles a fluid communication portal providing fluid communication between the reservoir and the fluid system.

4. The apparatus according to claim 1, wherein the wound contact fluid comprises a medicament to promote wound healing.

5. The apparatus according to claim 4, wherein the medicament comprises a debridement agent.

6. The apparatus according to claim 4, wherein the medicament comprises at least one of an antimicrobial agent, polyhexamethylene biguanide, an antibiotic, a growth factor and an analgesic.

7. The apparatus according to claim 1, wherein the fluid system comprises a syringe repeatably detachable from the apparatus.

* * * * *